(12) United States Patent
Ko et al.

(10) Patent No.: US 8,846,615 B2
(45) Date of Patent: *Sep. 30, 2014

(54) MNTF PEPTIDES

(75) Inventors: Pui-Yuk Dorothy Ko, Monterey Park, CA (US); Mark S. Kindy, Mt. Pleasant, SC (US)

(73) Assignee: Genervon Biopharmaceuticals, LLC, Pasadena, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 12/391,234

(22) Filed: Feb. 23, 2009

(65) Prior Publication Data
US 2009/0286747 A1 Nov. 19, 2009

Related U.S. Application Data

(60) Provisional application No. 61/066,669, filed on Feb. 21, 2008.

(51) Int. Cl.
 A01N 37/18 (2006.01)
 A61K 38/00 (2006.01)
 A61K 38/06 (2006.01)
 C07K 14/475 (2006.01)

(52) U.S. Cl.
 CPC ............. *C07K 14/475* (2013.01); *A61K 38/00* (2013.01)
 USPC ............ 514/8.3; 514/5.2; 514/7.6; 514/18.9; 514/18.2; 514/21.91; 514/21.9; 514/21.8; 530/330; 530/331; 530/332

(58) Field of Classification Search
 None
 See application file for complete search history.

(56) References Cited

U.S. PATENT DOCUMENTS

| 6,309,877 | B1 * | 10/2001 | Chau | 435/325 |
| 7,183,373 | B2 * | 2/2007 | Chau et al. | 530/300 |
| 7,507,713 | B2 * | 3/2009 | Chau | 514/1.1 |
| 8,334,253 | B2 * | 12/2012 | Ko | 514/1.1 |

* cited by examiner

Primary Examiner — Olga N Chernyshev

(57) ABSTRACT

The present invention relates to novel Motoneuronotrophic Factors (MNTF) peptides and analogs thereof, including compositions capable of promoting the growth and viability of neurons. MNTF peptides between two and six amino acids in length are provided, as well as analogs of these MNTF peptides that are modified by covalent attachment to another moiety. Other embodiments are described herein.

11 Claims, 1 Drawing Sheet

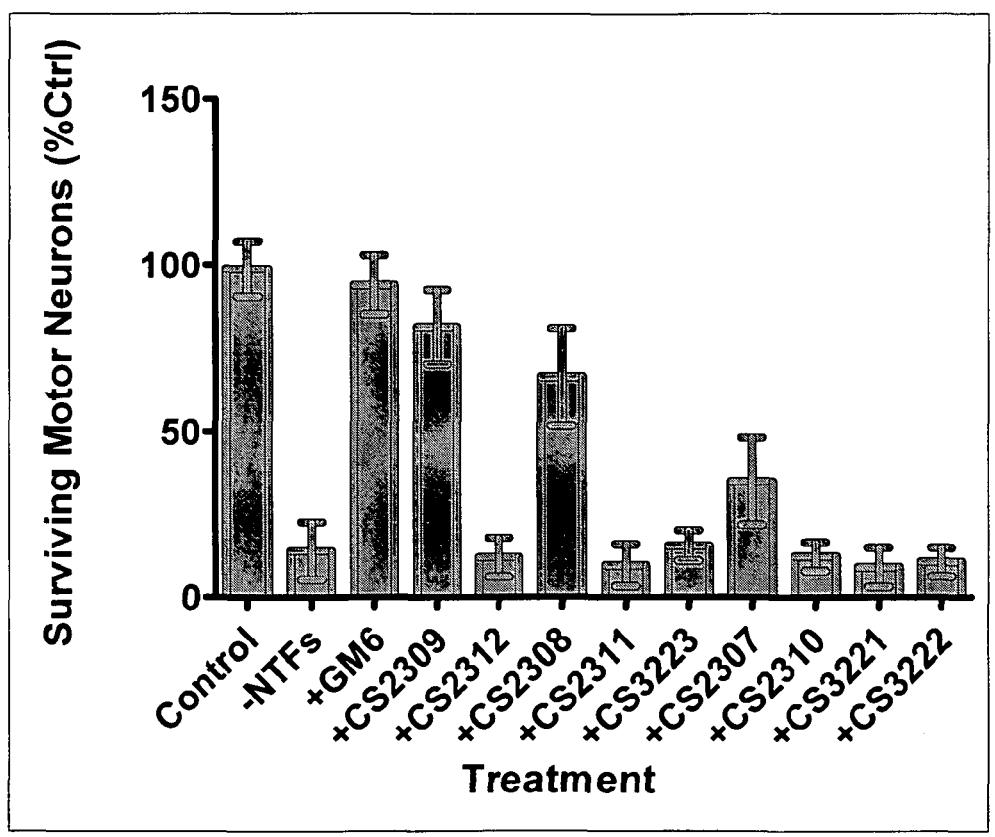

MNTF PEPTIDES

CROSS REFERENCE TO RELATED APPLICATIONS

This application claims priority from U.S. Provisional Application No. 61/066,669, filed Feb. 21, 2008 and entitled MNTF Peptide Compositions and Methods of Use, the contents of which is hereby incorporated by reference in its entirety.

FIELD

The present disclosure relates generally to compositions and methods for treating neuronal disorders using MNTF peptides and analogs thereof. Incorporated herein by reference is a compact disc containing a Sequence Listing, file name GNV007UT.txt, created on May11, 2009, file size 6 KB.

BACKGROUND

The following includes information that may be useful in understanding the present disclosure. It is not an admission that any of the information provided herein is prior art, or relevant, to the presently disclosure, or that any publication or document that is specifically or implicitly referenced is prior art.

The survival of embryonic motoneurons has been found to be dependent upon specific trophic substances derived from the associated developing skeletal muscles. Certain skeletal muscles have been reported to produce substances which are capable of enhancing the survival and development of motoneurons by preventing the embryonic motoneurons from degeneration and subsequent, natural cellular death. These substances have been broadly described as neuronotrophic factors (NTFs), which are a specialized group of proteins which function to promote the survival, growth, maintenance, and functional capabilities of selected populations of neurons (e.g. Chau, R. M. W., et al., 6 Chin. J Neuroanatomy 129, 1990).

A variety of neurodegenerative, neuromuscular and neuronal diseases, disorders, or conditions affecting the central and/or peripheral nervous systems may be characterized in whole or in part by acute or progressive loss of functional neural tissues.

U.S. Pat. Nos. 6,309,877, 7,183,373, 6,841,531, 6,759,389 and US20060052299 report specific neuronotrophic factors (NTFs) termed Motoneuronotrophic Factors (MNTF) which possesses the ability to exert trophic effects on motoneurons, the contents of which are hereby incorporated by reference in their entirety.

BRIEF SUMMARY

Described herein is technology having many attributes and embodiments including, but not limited to, those set forth or described or referenced in this Brief Summary. It is not intended to be all-inclusive and the claims are not limited to or by the features or embodiments identified in this Brief Summary, which is included for purposes of illustration only and not restriction.

Accordingly, in one aspect, the present disclosure is directed to novel peptides and compositions containing portions of the MNTF-molecule that are useful for modulating the viability and proliferation of neuronal cells, thereby providing for neurotrophic peptides that can be readily synthesized and therapeutically efficacious in treating a wide range of neurodegenerative, neuromuscular diseases, disorders, or conditions in the central and/or peripheral nervous systems.

In one aspect, the present disclosure is directed to synthetic and/or purified MNTF peptides or analogs thereof comprising at least two consecutive residues, include the FS (SEQ ID No: 3) residues at positions 17 and 18 of LGTFWGDTLN CWMLSAFSRY ARCLAEGHDG PTQ (SEQ ID NO: 1), useful for inducing or modulating the viability and growth of a neuronal cell.

In certain embodiments, a MNTF peptide or analog thereof includes sequence analogs comprising SEQ ID NOS: 1-22. In certain embodiments, the MNTF peptide or analog thereof is a 2-mer, a 3-mer, a 4-mer, or a 5-mer non-palmitylated peptide. In certain other embodiments, the MNTF peptide or analog thereof is a 2-mer, a 3-mer, a 4-mer, a 5-mer or a 6-mer palmitylated peptide. In certain aspects, the disclosure provides a composition comprising a MNTF peptide or an analogue thereof that is N-terminally modified by covalent bonding/linkage or conjugation with a penetration enhancer or by adding the penetration enhancer via peptide bonding during solid phase synthesis.

In certain embodiments, an MNTF peptide consists of i) between 2 and 6 consecutive amino acids of SEQ ID NO: 1; ii) between 2 and 5 consecutive amino acids of SEQ ID NO: 1; iii) between 3 and 5 consecutive amino acids of SEQ ID NO: 1; iv) at least 2 consecutive amino acids of SEQ ID NO: 1; v) at least 3 consecutive amino acids of SEQ ID NO: 1, or vi) an analog of any thereof, such as a functional derivative of any of i)-v). The MNTF peptide in i), iv) and v) does not have an amino acid sequence consisting of SEQ ID NO: 2. In certain other embodiments, MNTF peptide or analog thereof have an amino acid sequence selected from the group consisting of SEQ ID NO:3-SEQ ID NO:22 or a functional derivative thereof. Preferred MNTF peptides or analogs have MNTF activity.

In some aspects, the MNTF peptide analog is covalently attached (e.g., by peptide bonding at the N-terminus) to a fatty acid molecule of 2 to 22 carbons (e.g. palmitic acid). In one aspect, the disclosure provides a dermopharmaceutical composition comprising a peptide having at least 2 contiguous amino acids residues including FS (SEQ ID No: 3) selected from LGTFWGDTLNCWMLSAFSRYARCLAEGHDGPTQ (SEQ. ID. NO. 1) or an analog thereof and a pharmaceutically acceptable carrier.

In some embodiments, the MNTF peptide or analog thereof comprises the phenylalanine-serine dipeptide of SEQ ID NO: 1 and from 1-30 additional amino acids of SEQ ID NO: 1, said MNTF peptide or analog thereof optionally having from 1-5 conservative amino acid substitutions of the sequence depicted in SEQ ID NO: 1, or an ester, amide, prodrug and/or salt form thereof.

In another embodiment, the MNTF peptide analog is conjugated or covalently attached or by peptide bonding at the N-terminal to a fatty acid molecule of 2 to 22 carbons (e.g. palmitic acid) to enhance skin penetration and/or oil solubility.

```
LGTFWGDTLN CWMLSAFSRY     (SEQ ID NO: 1)
ARCLAEGHDG PTQ

FSRYAR                    (SEQ ID NO: 2)

FS                        (SEQ ID NO: 3)

FSR                       (SEQ ID NO: 4)
```

| | |
|---|---|
| AFS | (SEQ ID NO: 5) |
| FSRY | (SEQ ID NO: 6) |
| SAFS | (SEQ ID NO: 7) |
| AFSR | (SEQ ID NO: 8) |
| LSAFS | (SEQ ID NO: 9) |
| SAFSR | (SEQ ID NO: 10) |
| AFSRY | (SEQ ID NO: 11) |
| FSRYA | (SEQ ID NO: 12) |
| MLSAFS | (SEQ ID NO: 13) |
| LSAFSR | (SEQ ID NO: 14) |
| SAFSRY | (SEQ ID NO: 15) |
| AFSRYA | (SEQ ID NO: 16) |
| SRYAR | (SEQ ID NO: 17) |
| RYAR | (SEQ ID NO: 18) |
| YAR | (SEQ ID NO: 19) |
| SRYA | (SEQ ID NO: 20) |
| RYA | (SEQ ID NO: 21) |
| SRY | (SEQ ID NO: 22) |

In another aspect, compositions and methods are provided for modulating the viability and/or growth of a neuronal cells by administering the MNTF peptide or analog thereof in vitro to cell cultures or in vivo to an individual suffering from a nerve injury or neurodegenerative disorder, in order to promote cell proliferation or stabilize inappropriate cell death, and/or in either case to restore normal cell behavior. In another aspect, there is provided a method of improving motor function in a subject with symptoms of neural pathway damage comprising administering a motoneuronotropic factor (MNTF) peptide or analog thereof to the subject in need thereof.

Accordingly, in one aspect, the present disclosure is directed to novel peptides and compositions containing portions of the MNTF-molecule that are useful for modulating the viability and proliferation of neuronal cells, thereby providing for neurotrophic peptides that can be readily synthesized and therapeutically efficacious in treating a wide range of skin disorders, including the reinnervation of nerves and muscles in the area below the skin.

In one aspect, the present disclosure is directed to synthetic and/or purified MNTF peptide or analog thereof comprising the FS (SEQ ID No: 3) domain useful for inducing or modulating the viability and growth of a neuronal cell in close proximity to the skin.

In another aspect, compositions and methods for modulating the viability and/or growth of a neuronal cells by administering the MNTF peptide or analog thereof in vitro to cell cultures or in vivo to an individual suffering from a nerve injury or neurodegenerative disorder, in order to promote cell proliferation or stabilize inappropriate cell death, and/or in either case to restore normal cell behavior.

In one aspect, there is provided a method of repairing a damaged neural pathway in a subject comprising administering a MNTF peptide or analog thereof to the subject in need thereof, wherein said damaged neural pathway is associated with a skin injury or condition, wherein said MNTF peptide or analog thereof is administered in an amount sufficient to treat said skin condition or disorder whereby the damaged neural pathway in said subject is repaired.

DESCRIPTION OF THE FIGURES

FIG. 1. Illustrates a survival assay of exemplary MNTF peptides on motor neuron survival. Motor neurons were cultured from rat spinal cords and grown in culture for 3 days in the presence of BDNF, GDNF and CNTF. After 3 days, the cells were grown in the absence of the conventional trophic factors but with the indicated MNTF peptides at 10 microgram/ml. After 48 hours the number of live cells was determined. The graph indicates mean+/−SD of five samples (BDNF=Brain derived neurotrophic factor; GDNF=Glial derived neurotrophic factor; CNTF=Ciliary neurotrophic factor).

DETAILED DESCRIPTIONS

The survival of embryonic motoneurons has been found to be dependent upon specific trophic substances derived from the associated developing skeletal muscles. Skeletal muscles have been reported to produce substances which are capable of enhancing the survival and development of motoneurons by preventin, the embryonic motoneurons from degeneration and subsequent, natural cellular death, (O'Brian, R. J and Fischbach, G. D., 6 J. Neurosci 3265 (1986); Hollyday, M. and Hamburger, V., 170 J. Comp. Neurol. 311 ('1976'). McManaman. J. L., et al, 263 J. Biol. Chem. 5890 (1988); Oppenheim, R. W., et al, 240 Science, 919 (1988); and Smith, R. G., et al., 6 J. Neurosci. 439 (1986).

Human Motoneuronotrophic Factor (MNTF) is a specific NTF derived from skeletal muscle tissue that has been shown to reduce inflammation at the site of motoneuron injury, enhance nerve regeneration, and promote the survival of motoneurons. MNTF has been tested in various rat nerve systems, including the peripheral sciatic nerve (controlling lower limb muscles), the peripheral musculocutaneous nerve (controlling upper limb muscles), the cranial facial nerve (controlling facial and head muscles), the cranial hypoglossal nerve (controlling the tongue), and the portion of the spinal cord that controls muscles in the neck, chest and upper limbs. In the spinal cord model, MNTF was applied on the nerve graft in a hemi-section spinal cord in rat; MNTF reduced inflammation, limited degeneration and enhanced regeneration of the grafted nerves. A number of studies have demonstrated the efficacy of the synthesized MNTF or peptide analogs described therein in rat peripheral nerve model systems for trophic and tropic effects when applied directly on the nerve. In addition, MNTF has been shown to promote the regeneration and survival of motoneurons.

Neuronal cell death occurs in the nervous systems of vertebrates during certain periods of growth and development. Thus, addition of soluble neuronal trophic factors from associated target tissues can serve to mitigate this phenomenon of neuronal death.

Accordingly, aspects and embodiments of the present disclosure provide methods and compositions comprising the MNTF peptide or analog thereof for the treatment of neuronal disorders.

Aspects and embodiments of the disclosure are directed to a functional protein domain associated with the actions of motoneuronotrophic factors, which has been identified and mapped to short overlapping subsequences in the MNTF molecule. These protein domains, which include the domains in SEQ ID NOS: 2-22, are sufficient to modulate the viability and proliferation of neuronal cells. Moreover, truncated MNTF peptides or analogs encompassing these domains are themselves sufficient to demonstrate stimulatory bioactivity in motoneuron/neuroblastoma cell hybrids.

Definitions

Certain terms used in the context of the describing the technology to which this disclosure pertains are set forth. Unless indicated otherwise, the following terms have the following meanings when used herein and in the appended claims. Those terms that are not defined below or elsewhere in the specification shall have their art-recognized meaning.

As used herein, a "motoneuronotrophic factor or motoneuron trophic factor" includes those factors involved in the nutrition or maintenance of motor neurons. The terms "motoneuronotropic factor", "MNTF", "MNTF peptide", "motoneuronotropic factor analog", and "MNTF analog" refer to peptides and analogs thereof, respectively, as described herein and having the functional properties defined herein. These may include sequence and functional homologs of the reference MNTF sequence. Motoneuronotrophic factors may further the development and differentiation of committed neural progenitor cells, or they may induce or enhance the growth (e.g. neurite outgrowth) and survival of differentiated neural cells. "MNTF activity" includes one or more of the following activities: promoting the growth of neurons, promoting the maintenance of neurons, promoting neurite outgrowth, promoting axonal regeneration of an axotomized motoneurons, improving motor function, repairing damaged neural pathway, regenerating a neural pathway, or alleviating a neuronal defect. The motoneuronotrophic factors of the present disclosure are typically provided in amounts effective to produce a fully-differentiated neural cell of the CNS or PNS (e.g., a motor neuron). Guidance for the amount is provided herein, and may be readily determined by the skilled artisan based upon known procedures and methods disclosed herein.

MNTF peptides have been reported in Chau, R. M. W., et al., Muscle Neuronotrophic Factors Specific for Anterior Horn Motoneurons of Rat Spinal Cord. In: Recent Advances in Cellular and Molecular Biology, Vol. 5, Peeters Press, Leuven, Belgium, pp. 89-94 (1992), as well as those found in for example, U.S. Pat. Nos. 6,309,877, 7,183,373, 6,841,531, 6,759,389 and US20060052299, the contents of which are hereby incorporated in their entirety. In certain embodiments, exemplars include synthetic and/or purified MNTF peptides or analogs thereof comprising a portion of the domains from SEQ ID NOS: 2-22 and to molecules that mimic the structure and/or function thereof, including truncated sequence homologs and analogs, useful for inducing or modulating the viability and growth of a neuronal cell.

In addition, MNTF peptides may also include those described in Chau, R. M. W., et al., The Effect of a 30 kD Protein from Tectal Extract of Rat on Cultured Retinal Neurons, 34 Science in China, Series B, 908 (1991); Chau, R. M. W., et al., Muscle Neuronotrophic Factors Specific for Anterior Horn Motoneurons of Rat Spinal Cord. In: Recent Advances in Cellular and Molecular Biology, Vol. 5, Peeters Press, Leuven, Belgium, pp. 89-94 (1992); Chau, R. M. W., et al., The Effect of a 30 kD Protein from Tectal Extract of Rat on Cultured Retinal Neurons, 34 Science in China, Series B, 908 (1991); Chau, R. M. W., et al., Cloning of Genes for Muscle-Derived Motoneuronotrophic Factor 1 (MNTF1) and Its Receptor by Monoclonal Antibody Probes, (abstract) 19 Soc. for Neurosci. part 1, 252 (1993), Chau, R. M. W., et al., Cloning of Genes for Muscle-Derived Motoneuronotrophic Factor 1 (MNTF1) and Its Receptor by Monoclonal Antibody Probes, (abstract) 19 Soc. for Neurosci. part 1, 252 (1993), the entire contents of which is hereby incorporated by reference.

In certain embodiments, a MNTF peptide or analog thereof may include sequences from one of the active sites of the MNTF domain (e.g. an MNTF peptide of two amino acids, such as SEQ ID NO: 3).

In certain embodiments, the MNTF peptide consists of a sequence described in SEQ ID NOs: 2-22. In other embodiments, the MNTF peptide analogs include functional derivatives of the MNTF peptides depicted in SEQ ID NOs: 2-22.

MNTF peptides and analogs thereof described herein include peptides derived from MNTF (i.e., from SEQ ID NO: 1), and functional derivatives thereof. These compounds include peptides having the amino acid sequence of one of SEQ ID NOs: 2-22, and functional derivatives of peptides having the amino acid sequences provided in SEQ ID NOs: 2-22.

"Analogs" as used in the present application includes peptides which have been modified but retain MNTF activity (e.g. by truncation, substitution, covalent attachment to another moiety, etc. relative to a 33 mer MNTF, SEQ ID NO: 1). MNTF peptide analogs include, for example, esters, amides, prodrugs, and salt forms of MNTF peptides. MNTF peptide analogs include MNTF peptides that have been covalently modified by attachment to another moiety, such as for example a MNTF peptide covalently linked to a lipophilic moiety (e.g. a fatty acid), a carrier molecule, or a heterologous polypeptide to produce a fusion protein. In certain embodiments, analogs in accordance with the present disclosure include "conservative" substitutions (e.g. relative to SEQ ID NO: 1). Conservative amino acid substitutions include amino acids replacements with synonymous amino acids within the same group, which have sufficiently similar physicochemical properties that substitution between members of the group will preserve the biological function of the molecule, Grantham, Science, Vol. 185, pp. 862-864 (1974). MNTF analogs further encompass MNTF functional derivatives of the peptides or analogs described herein. In some embodiments, the MNTF analogs may include 20%, 25%, 30%, 35% or up to 40% conservative amino acid substitutions as compared with the sequence depicted in SEQ ID NO: 1 or truncated versions thereof, including SEQ ID NOs:2-22.

As used herein "functional derivatives" of MNTF refer to derivatives which can be prepared from the functional groups present on the lateral chains of the amino acid moieties or on the terminal N- or C-groups according to known methods and are comprised in the disclosure when they are pharmaceutically acceptable i.e. when they do not destroy the protein/peptide activity or do not impart unacceptable toxicity to the pharmaceutical composition containing them. Such derivatives may include, for example, aliphatic esters or amides of the carboxyl-groups and N-acyl derivatives of free amino groups, as well as O-acyl derivatives of free hydroxyl-groups and are formed with acyl-groups as for example alcanoyl- or aroyl-groups, prodrugs, salts of functional groups, or having a combination thereof.

The synonymous amino acid groups include those defined in Tables I, II, and III.

TABLE I
Broader Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II
Intermediate Groups of Synonymous Amino Acids

| Amino Acid | Synonymous Group |
|---|---|
| Ser | Ser |
| Arg | His, Lys, Arg |
| Leu | Ile, Phe, Met, Leu |
| Pro | Ala, Pro |
| Thr | Thr |
| Ala | Pro, Ala |
| Val | Met, Ile, Val |
| Gly | Gly |
| Ile | Ile, Met, Phe, Val, Leu |
| Phe | Met, Tyr, Ile, Leu, Phe |
| Tyr | Phe, Tyr |
| Cys | Ser, Cys |
| His | Arg, Gln, His |
| Gln | Glu, His, Gln |
| Asn | Asp, Asn |
| Lys | Arg, Lys |
| Asp | Asn, Asp |
| Glu | Gln, Glu |
| Met | Phe, Ile, Val, Leu, Met |
| Trp | Trp |

TABLE III
Narrower Groups of Synonymous Amino Acids

| Amino Acid | Synonymous Group |
|---|---|
| Ser | Ser |
| Arg | Arg |
| Leu | Ile, Met, Leu |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Ser, Cys |
| His | His |
| Gln | Gln |
| Asn | Asn |
| Lys | Lys |
| Asp | Asp |
| Glu | Glu |
| Met | Ile, Leu, Met |
| Trp | Trp |

Amino acids used in compounds provided herein (e.g., peptides and proteins) can be genetically encoded amino acids, naturally occurring non-genetically encoded amino acids, or synthetic amino acids. Both L- and D-enantiomers of any of the above can be utilized in the compounds. The following abbreviations may be used herein for the following genetically encoded amino acids (and residues thereof): alanine (Ala, A); arginine (Arg, R); asparagine (Asn, N); aspartic acid (Asp, D); cysteine (Cys, C); glycine (Gly, G); glutamic acid (Glu, E); glutamine (Gln, Q); histidine (His, H); isoleucine (Ile, I); leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V).

Certain commonly encountered amino acids that are not genetically encoded and that can be present in the compounds described herein include, but are not limited to, β-alanine (b-Ala) and other omega-amino acids such as 3-aminopropionic acid (Dap), 2,3-diaminopropionic acid (Dpr, Z), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle, J); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys); 3-benzothiazol-2-yl-alanine (BztAla, B); and homoserine (hSer). Additional amino acid analogs contemplated include phosphoserine, phosphothreonine, phosphotyrosine, hydroxyproline, gamma-carboxyglutamate, hippuric acid, octahydroindole-2-carboxylic acid, statine, α-methylalanine, para-benzoyl-phenylalanine, propargylglycine, and sarcosine. Peptides described herein can have any of the foregoing amino acids in the L- or D-configuration, or any other amino acid described herein or known in the art, whether currently or in the future.

Amino acids that are substitutable for each other generally reside within similar classes or subclasses. As known to one of skill in the art, amino acids can be placed into different classes depending primarily upon the chemical and physical properties of the amino acid side chain. For example, some amino acids are generally considered to be hydrophilic or polar amino acids and others are considered to be hydrophobic or nonpolar amino acids. Polar amino acids include amino acids having acidic, basic or hydrophilic side chains and nonpolar amino acids include amino acids having aromatic or hydrophobic side chains. Nonpolar amino acids may be further subdivided to include, among others, aliphatic amino acids. The definitions of the classes of amino acids as used herein are as follows:

"Nonpolar Amino Acid" refers to an amino acid having a side chain that is uncharged at physiological pH, that is not polar and that is generally repelled by aqueous solution. Examples of genetically encoded hydrophobic amino acids include Ala, Ile, Leu, Met, Trp, Tyr and Val. Examples of non-genetically encoded nonpolar amino acids include t-BuA, Cha and Nle.

"Aromatic Amino Acid" refers to a nonpolar amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 3-benzothiazol-2-yl-alanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Aliphatic Amino Acid" refers to a nonpolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Polar Amino Acid" refers to a hydrophilic amino acid having a side chain that is charged or uncharged at physiological pH and that has a bond in which the pair of electrons shared in common by two atoms is held more closely by one of the atoms. Polar amino acids are generally hydrophilic, meaning that they have an amino acid having a side chain that is attracted by aqueous solution. Examples of genetically encoded polar amino acids include asparagine, cysteine, glutamine, lysine and serine. Examples of non-genetically encoded polar amino acids include citrulline, homocysteine, N-acetyl lysine and methionine sulfoxide.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include ornithine, 2,3-diaminopropionic acid, 2,4-diaminobutyric acid and homoarginine.

"Ionizable Amino Acid" refers to an amino acid that can be charged at a physiological pH. Such ionizable amino acids include acidic and basic amino acids, for example, D-aspartic acid, D-glutamic acid, D-histidine, D-arginine, D-lysine, D-hydroxylysine, D-ornithine, L-aspartic acid, L-glutamic acid, L-histidine, L-arginine, L-lysine, L-hydroxylysine or L-ornithine.

As will be appreciated by those having skill in the art, the above classifications are not absolute. Several amino acids exhibit more than one characteristic property, and can therefore be included in more than one category. For example, tyrosine has both a nonpolar aromatic ring and a polar hydroxyl group. Thus, tyrosine has several characteristics that could be described as nonpolar, aromatic and polar. However, the nonpolar ring is dominant and so tyrosine is generally considered to be nonpolar. Similarly, in addition to being able to form disulfide linkages, cysteine also has nonpolar character. Thus, while not strictly classified as a hydrophobic or nonpolar amino acid, in many instances cysteine can be used to confer hydrophobicity or nonpolarity to a peptide.

In some embodiments, polar amino acids as contemplated herein may include, for example, arginine, asparagine, aspartic acid, cysteine, glutamic acid, glutamine, histidine, homocysteine, lysine, hydroxylysine, ornithine, serine, threonine, and structurally related amino acids. In one embodiment the polar amino is an ionizable amino acid such as arginine, aspartic acid, glutamic acid, histidine, hydroxylysine, lysine, or ornithine.

Examples of polar or nonpolar amino acid residues that can be utilized include, for example, alanine, valine, leucine, methionine, isoleucine, phenylalanine, tryptophan, tyrosine and the like.

The term "salts" herein refers to both salts of carboxyl groups and to acid addition salts of amino groups of the peptides described herein or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid salts include, for example, salts with mineral acids such as, for example, hydrochloric acid or sulphuric acid, and salts with organic acids such as, for example, acetic acid or oxalic acid. Of course, any such salts must retain the activity of the peptides disclosed herein or their analogs.

The "precursors" are compounds which are converted into the peptides disclosed herein in the human or animal body.

The peptides of the present disclosure may be prepared by any well known procedure in the art, such as solid phase synthesis or liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their α-amino groups and side chain functional groups protected with appropriate protective groups are condensed one by one in order from the C-terminus to the N-terminus, and one where the amino acids bound to the resin or the protective group of the α-amino groups of the peptides are released, the peptide chain is thus extended in this manner. Solid phase synthesis methods are largely classified by the tBoc method and the Fmoc method, depending on the type of protective group used.

Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; $NO_2$ (nitro) and Pmc (2,2,5,7,8-pentamethylchromane-6-sulphonyl) for the guanidino groups); and tBu (t-butyl) for the hydroxyl groups).

After synthesis of the desired peptide, it is subjected to the de-protection reaction and cut out from the solid support. Such peptide cutting reaction may be carried with hydrogen fluoride or trifluoromethane sulfonic acid for the Boc method, and with TFA for the Fmoc method.

The crude peptide thus obtained is then subjected to purification. Purification is carried out by any one of the methods known for this purpose, i.e. any conventional procedure involving extraction, precipitation, chromatography, electrophoresis, or the like. For example, HPLC (high performance liquid chromatography) can be used. The elution can be carried using a water-acetonitrile-based solvent commonly employed for protein purification.

The peptide described herein can be provided in substantially purified form, in order to be suitable for use in pharmaceutical compositions, as active ingredient, in pathologies that require MNTF activity and/or modulation thereby.

As used herein, the terms "biologically active peptide" and "biologically active fragment" refer to a peptide or polypeptide in accordance with the above description of motoneuron differentiation factors (MNDF) and/or motoneuronotrophic factors (MNTF) wherein the MNDF differentiates stem cells into motor neurons and the MNTF wherein MNTF exhibits neural protection, repair and therapeutic functions.

As used herein, the exemplary MNTF peptides and analogs thereof include those demonstrated herein to be sufficient for the differentiation of stem cells into motor neurons.

As used herein, "preventing" means preventing in whole or in part, or ameliorating or controlling.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented.

As used herein, an "effective amount" in reference to the compounds or compositions described herein refers to the amount sufficient to induce a desired biological, pharmaceutical, or therapeutic result. That result can be alleviation of the signs, symptoms, or causes of a disease or disorder or condition, or any other desired alteration of a biological system.

The phrase "percent (%) identity" refers to the percentage of sequence similarity found in a comparison of two or more sequences. Percent identity can be determined electronically using any suitable software, for example. Likewise, "similarity" between two sequences (or one or more portions of either or both of them) is determined by comparing the sequence of one sequence to a second sequence.

As described herein, the terms "homology and homologues" may include peptides containing amino acid sequence homologies to the protein sequence of interest. Such peptide typically has at least about 70% homology, and can be at least about 80%, 90%, 95%, 97% or 99% homology with the relevant sequence, for example over a region of at least about 15, 20, 30, 40, 50, 100 more contiguous amino acid/polypeptide of the homologous sequence. They may further comprise up to about 25%, 30%, 40% or 50% conservative amino acid changes relative to a reference sequence (e.g. SEQ ID NO: 1), depending on the length of the peptide and the reference sequence.

General Aspects of Treatment

Methods of treating a subject with a neuronal disorder comprising administering to the subject a motoneuronotropic factor (MNTF) peptide or analog thereof is provided.

As used herein, neuronal disorder may include disease, disorder or conditions associated with or characterized in whole or in part by acute, progressive or gradual loss of functional neural tissue.

A "neurodegenerative disease" refers to a condition associated with central or peripheral nervous system characterized by progressive, gradual, loss of functional neural tissue.

Overview

The isolation and characterization of two motoneuronotrophic factors (MNTF1 and MNTF2) from rat muscle tissues as well as the subsequent cloning of a recombinant MNTF1-F6 gene derived from a human retinoblastoma cDNA library, is described in U.S. Pat. Nos. 6,309,877, 6,759,389 and 6,841,531 (as well as co-pending U.S. patent application Ser. Nos. 10/858,144, 10/858,286, 10/858,543 and 10/858,545); all of which are hereby incorporated by reference in their entirety. The MNTF1-F6 gene sequence encodes a 33 amino acid MNTF1 polypeptides which was found to map within human chromosome 22q22, as described in International Application No. PCT/US2004/038651, which is hereby incorporated by reference in its entirety.

Two overlapping domains within the MNTF1-F6 molecule that appear to be sufficient for the known biological activities of MNTF1 were identified. See, International Application Ser. No. PCT/US04/01468 or U.S. patent application Ser. No. 10/541,343, issued as U.S. Pat. No. 7,183,373, which are hereby incorporated by reference in their entirety. Each of these domains, designated herein as the "WMLSAFS" (SEQ ID No: 23) and "FSRYAR" (SEQ ID No: 2) domains, were sufficient to stimulate the proliferation of motor neuron derived cell lines in a manner similar to the MNTF1-F6 33-mer. Similarly, the "FSRYAR" (SEQ Id No: 2) domain is sufficient to direct selective re-enervation of muscle targets by motor neurons in vivo in a manner similar to the MNTF1-

F6 33-mer. In addition, the "FSRYAR" (SEQ ID No: 2) domain provides an antigenic epitope that, when used to provoke an immune response, is sufficient to generate an antibody that recognizes MNTF peptides containing the "FSRYAR" (SEQ ID No: 2) sequence, including the MNTF1-F6 33-mer.

Furthermore, as described herein, MNTF peptides that include at least two consecutive residues of SEQ ID NO: 1 can be used as described herein, provided that the peptides include at least the phenylalanine and serine residues present at positions 17 and 18, respectively, of SEQ ID NO: 1.

Motoneuron Trophic Factor (MNTF) peaks in expression during week 9 in human fetus gestation period (Di, X. et al., Acta Anatomica Sinica 29:86-89, 1998). Based on the expression of MNTF in the developing human, we reasoned that MNTF may promote the differentiation and/or survival of motoneurons.

Methods of Use

MNTF1 and/or its peptide analogs promote the survival of mammalian motor neurons in vitro. Accordingly, the technology described herein provides for the use of an MNTF peptide or analog thereof as a growth factor/supplement for neuronal cell cultures, including a method for promoting the survival of stem cell derived neuronal cell lines, by cultivating stem cell derived neuronal cells in vitro with an effective amount of a MNTF peptide or analog thereof.

Other MNTF peptides have shown efficacy in differentiation of stem cell as described in U.S. patent application Ser. No. 12/093,452, PCT/US06/043874. MNTF peptides provided herein have similar biological activities and therefore will modulate the differentiation of pluripotent embryonic stem cells into motoneurons and enhance the survival of ES cell-derived motoneurons. The exposure of ES cells to RA and MNTF analogs directs these cells to generate motor neurons.

MNTF and truncated MNTF molecules, include but not limited to those comprise ng the MLSAFSRYAR (SEQ ID No: 24)domain, referred to as a motor neuron differentiation factors (MDNF), demonstrated in U.S. patent application Ser. No. 12/093,452, PCT/US06/043874 to induce differentiation of stem cells or partially differentiated neuronal cells into motor neurons. Such agents provide a novel method for generating and/or isolating a population of motor neurons from stem cell cultures.

The method comprises contacting an embryonic stem cell with retinoic acid (RA) and a motor neuron differentiation factor (MNDF). In an embodiment described herein, the embryonic stem cell is contacted with RA concomitantly with the motor neuron differentiation factor. Alternatively, the method comprises contacting a partially differentiated neuronal cell with a motor neuron differentiation factor. The factors are provided in amounts effective to produce a differentiated neural cell. These amounts may be readily determined by the skilled artisan, based upon known procedures and methods disclosed herein.

The differentiated motor neurons can be isolated or enriched, e.g. by FACS sorting. For example the use of a GFP-based motor neuron marking method permits the characterization of pure populations of ES-cell-derived motor neurons. We have employed this protocol for isolating pure motoneuron population of cells from a mixed population of cells from embryoid bodies. Embryoid bodies are disaggregated to single cells using collagenase and dispase. These single cells are then FACS sorted for GFP, since cells expressing GFP controlled by an HB9 promoter are the true motoneurons in the population.

Accordingly, another aspect of the technology is directed to a method for isolating and/or purifying a population of differentiated neural cells by: (a) obtaining or generating a culture of embryonic stem cells that express enhanced green fluorescent protein (eGFP) under the control of a motor neuron specific promoter; (b) contacting the culture of embryonic stem cells with an amount of a RA and MNTF effective to produce differentiated neural cells that express eGFP; (d) detecting expression of eGFP in the differentiated neural cells; and (f) isolating the differentiated neural cells that express eGFP.

MNTF Peptides and Analogs Thereof

As those of skill familiar with the art and the disclosure will appreciate, sequences comprising the MNTF active domain and peptide analogs thereof can impart neural protection, repair and therapeutic functions on motorneurons in vitro and in vivo. The MNTF factors described herein may be produced synthetically or recombinantly, or isolated from native cells.

The sequence of amino acid residues in a protein or peptide comprising the MNTF peptide or analog thereof of the present disclosure are designated herein either through the use of their commonly employed three-letter designations or by their single-letter designations. A listing of these three-letter and one-letter designations may be found in textbooks such as Biochemistry, Second Edition, Lehninger, A., Worth Publishers, New York, N.Y. (1975). When the amino acid sequence is listed horizontally, the amino terminus is intended to be on the left end whereas the carboxy terminus is intended to be at the right end.

It will be appreciated by those of skill that the precise chemical structure of peptides comprising the various MNTF peptide or analog thereof will vary depending upon a number of factors. For example, a given polypeptide may be obtained as an acidic or basic salt, or in neutral form, since ionizable carboxyl and amino groups are found in the molecule. For the purposes of the disclosure, then, any form of the peptides comprising the sequences/domains listed in SEQ ID NOS: 2-22, which retains a biological activity of the MNTF peptide, is intended to be within the scope of the technology described herein. In certain embodiments, the disclosure includes peptide compositions consisting essentially of the sequences/domains listed in SEQ ID NOS: 2-22, which retains a biological activity of the MNTF peptide.

The present disclosure includes the use of MNTF peptide analogs that retain the ability of MNTF to exert neuro-protection, promote survival, maintenance and/or repair of motorneurons; or in certain instances, to differentiate stem cells into motor neurons.

To compare a polypeptide sequence with the corresponding SEQ ID NO: 1 fragment, a global alignment of the sequences can be performed using the BLAST programs publicly available through the National Center for Biotechnology Information (on the World Wide Web at ncbi.nlm.nih.gov). Prior to performing a global alignment, SEQ ID NO: 1 can be submitted to GenBank. Default parameters provided by the National Center for Biotechnology Information can be used for a global alignment.

It is to be understood that the technology described herein includes use of peptide analogs in which one or more amino acids can be substituted with other amino acids. In some embodiments, the motoneuronotrophic factor peptide analog contains one or more conservative amino acid substitutions to a fragment of at least 2 consecutive amino acid residues of SEQ ID NO: 1. In certain embodiments, the 2 consecutive amino acid residues are F-S.

The rational design of MNTF and other analogous domain mimetics or binding molecules, based on modeled (or experimentally determined) peptide structure, may be carried out by those of skill, using known methods of rational drug design. The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

The three-dimensional MNTF molecule and related structures disclosed herein can be used in computerized rational drug design (i.e., molecular modeling and molecule-molecule interaction modeling) methods to identify candidate compounds that bind with an active portion of MNTF. A variety of computerized drug design programs capable of modeling the interaction of a candidate compound with, for example, atomic coordinates described herein, are known in the art, and the operation of such programs is within the knowledge of the ordinary artisan in the field of rational drug design.

Methods of Making

It is understood that a composition comprising an MNTF peptide or analog thereof of the present disclosure may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an MNTF peptide or analog thereof described herein in an in vitro translation system or in a living cell. The MNTF peptide or analog thereof of the composition can be isolated and extensively dialyzed to remove one or more undesired small molecular weight molecules and/or lyophilized for more ready formulation into a desired vehicle. It is further understood that additional amino acids, mutations, chemical modification and such like, if any, that are made in a MNTF peptide component should not substantially interfere with receptor recognition of the MNTF docking sequence.

A peptide or polypeptide corresponding to one or more fragments of MNTF should generally be at least two amino acid residues in length, and may contain 2, 3, 4, or 5 amino acid residues. In certain embodiments, the MNTF peptide analog comprises 6 amino acid residues and a functional derivatization, e.g. a palmitylation. A peptide sequence may be synthesized by methods known to those of ordinary skill in the art, such as, for example, peptide synthesis using automated peptide synthesis machines, such as those available from Applied Biosystems (Foster City, Calif.). The technology described herein includes synthesis and use of cyclic peptides derived from SEQ ID NOs: 1-22.

Covalent modifications can be introduced into a peptide by reacting targeted amino acid residues with an organic derivatizing agent that is capable of reacting with selected side chains or terminal residues. Covalent modification of polypeptides using organic derivatizing agents is well known to those of skill in the art. For example, cysteinyl residues can be reacted with α-haloacetates (and corresponding amines), such as chloroacetic acid or chloroacetamide, to give carboxymethyl or carboxyamidomethyl derivatives. Histidyl residues can be derivatized by reaction with diethylpyrocarbonate at pH 5.5-7.0, or with para-bromophenacyl bromide at pH 6 in 1 M sodium cacodylate. Lysinyl and amino terminal residues can be reacted with succinic or other carboxylic acid anhydrides. Arginyl residues can be modified by reaction with one or several conventional reagents, among them phenylglyoxal, 2,3-butanedione, 1,2-cyclohexanedione, and ninhydrin. Spectral labels can be introduced into tyrosyl residues by reaction with aromatic diazonium compounds or tetranitromethane; most commonly, N-acetylimidizol and tetranitromethane are used to form O-acetyl tyrosyl species and 3-nitro derivatives, respectively. Carboxyl side groups (aspartyl or glutamyl) can be selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions. Glutaminyl and asparaginyl residues can be deamidated to the corresponding glutamyl and aspartyl residues. Other modifications include hydroxylation of proline and lysine, phosphorylation of hydroxyl groups of seryl or threonyl residues, methylation of the α-amino groups of lysine, arginine, and histidine side chains (T. E. Creighton, 1983, Proteins: Structure and Molecule Properties, W.H. Freeman & Co., San Francisco, pp. 79-86), acetylation of the N-terminal amine, and, in some instances, amidation of the C-terminal carboxyl groups.

The MNTF peptides or analogs thereof described herein can be used in assays and kits for assays, either in the free form or linked to a carrier molecule such as a protein or a solid particle, as well as modified peptides linked to a label or tracer e.g. biotin or fluorescein isothiocyanate.

Crosslinking of an MNTF peptide or analog thereof to a water-insoluble support matrix can be performed with bifunctional agents well known in the art including 1,1bis (diazoacetyl)2phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Bifunctional agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates can be employed for protein immobilization.

Crosslinking of a MNTF peptide or analog thereof to a second protein, including a second MNTF peptide or analog thereof, can be performed using the bifunctional reagents described herein. In some embodiments, there is inserted a spacer, for example a dithiol group or a diamino group or multiples of amino acid residues, e.g. glycine. The spacer may also be a homo- or hetero-bifunctional crosslinker, for example the heterobifunctional crosslinker N-(4-carboxy-cyclohexyl-methyl)-maleimide.

Longer peptides or polypeptides, e.g. a fusion protein, can be produced by standard recombinant DNA techniques. For example, a DNA fragment encoding a MNTF1 peptide fragment can be cloned in a commercially available expression vector that already contains a heterologous protein, with the result being MNTF1 peptide fragment fused in-frame to the heterologous protein.

In certain embodiments, a nucleic acid encoding an MNTF1 peptide and/or a component described herein may be used, for example, to produce a peptide in vitro or in vivo for the various compositions and methods described herein. For example, in certain embodiments, a nucleic acid encoding an MNTF1 peptide is a component of, for example, a vector in a recombinant cell. The nucleic acid may be expressed to produce a peptide or polypeptide comprising an MNTF1 peptide sequence. The peptide or polypeptide may be secreted from the cell, or as part of or within the cell.

Compound Screening

Compounds identified by the screening procedures described herein can further be distinguished, and the efficacy of the compound can be assessed, based upon their ability to treat neuronal disorders in art accepted animal cell culture disease and disorder model system. In many drug screening assays which test libraries of compounds and natural extracts, high throughput assays are desirable in order to maximize the number of compounds surveyed in a given period of time. Assays which are performed in cell-free systems, such as may be derived with purified or partially purified proteins, are often used as "primary" screens in that they can be generated to permit rapid development and relatively easy detection of an alteration in a molecular target which is mediated by a test compound. Further, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Thus in another aspect, a method of identifying a compound useful for promoting the growth or survival of motoneurons is provided. In one embodiment, the method comprises the steps of i) preparing a sample comprising a candidate compound, ii) contacting a cell with said sample, iii) determining whether the expression or activity of a compound involved in signal transduction pathway is modulated, and iv) determining whether the sample is capable of promoting the growth or survival of motorneurons. In other embodiments, the method further comprises determining whether a sample containing a candidate compound is regulated by a MNTF peptide or analog thereof, or alternatively regulated a MNTF peptide or analog thereof (e.g. activity, expression, etc.). In another aspect, the technology described herein includes methods of promoting the growth or survival of a motoneuron or for the treatment of a neuronal disorder by administering a compound identified by the screening procedures described herein.

In an exemplary screening assay, the compound of interest is contacted with a mixture including a MNTF binding protein (e.g., a cell expressing a MNTF peptide receptor) and a MNTF peptide under conditions in which it is ordinarily capable of binding a MNTF peptide. To the mixture is then added a composition containing a test compound. Detection and quantification of receptor/MNTF peptide complexes provides a means for determining the test compound's efficacy at inhibiting (or potentiating) complex formation between the receptor protein and the MNTF peptide. A control assay can also be performed to provide a baseline for comparison, in which isolated and purified MNTF peptide is added to the receptor protein and the formation of receptor/MNTF peptide complex is quantitated in the absence of the test compound.

Complex formation between the MNTF peptide and a MNTF peptide may be detected by a variety of techniques. For instance, modulation of the formation of complexes can be quantitated using, for example, detectably labeled proteins such as radiolabeled, fluorescently labeled, or enzymatically labeled MNTF peptides, by immunoassay, or by chromatographic detection. For cell-free assays, it will typically be desirable to immobilize either the MNTF peptide or the MNTF peptide binding protein to facilitate separation of receptor/MNTF peptide complexes from uncomplexed forms of one of the proteins, as well as to accommodate automation of the assay. For example, a fusion protein can be provided which adds a domain that allows the protein to be bound to a matrix. For example, glutathione-5-transferase/receptor (GST/receptor) fusion proteins can be adsorbed onto glutathione Sepharose beads (Sigma Chemical, St. Louis, Mo.) or glutathione derivatized microtiter plates, which are then combined with the MNTF peptide, e.g., an $^{35}$S-labeled MNTF peptide, and the test compound and incubated under conditions conducive to complex formation, e.g., at physiological conditions for salt and pH, though slightly more stringent conditions may be desired. Following incubation, the beads are washed to remove any unbound MNTF peptide, and the matrix bead-bound radiolabel determined directly (e.g., beads placed in scintillant), or in the supernatant after the complexes are dissociated. Alternatively, the complexes can be dissociated from the bead, separated by SDS-PAGE gel, and the level of MNTF peptide found in the bead fraction quantitated from the gel using standard electrophoretic techniques.

Other techniques for immobilizing proteins on matrices are also available for use in the subject assay. For instance, soluble portions of the MNTF peptide protein can be immobilized utilizing conjugation of biotin and streptavidin. For instance, biotinylated receptor molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the MNTF peptide but which do not interfere with ligand binding can be derivatized to the wells of the plate, and the receptor trapped in the wells by antibody conjugation. As above, preparations of a MNTF peptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the MNTF peptide, or which are reactive with the receptor protein and compete for binding with the MNTF peptide; as well as enzyme-linked assays which rely on detecting an enzymatic activity associated with the MNTF peptide. In the instance of the latter, the enzyme can be chemically conjugated or provided as a fusion protein with the MNTF peptide. To illustrate, the MNTF peptide can be chemically cross-linked or genetically fused with alkaline phosphatase, and the amount of MNTF peptide trapped in the complex can be assessed with a chromogenic substrate of the enzyme, e.g., paranitrophenylphosphate. Likewise, a fusion protein comprising the MNTF peptide and glutathione-5-transferase can be provided, and complex formation quantitated by detecting the GST activity using 1-chloro-2,4-dinitrobenzene (Habig et al., *J Biol Chem,* 249:7130 (1974)). For immunodetection for quantitating one of the proteins trapped in the complex, antibodies against the protein, such as the anti-MNTF peptide antibodies can be used. Alternatively, the protein to be detected in the complex can be "epitope tagged" in the form of a fusion protein which includes, in addition to the MNTF peptide or MNTF peptide sequence, a second polypeptide for which antibodies are readily available (e.g., from commercial sources). For instance, the GST fusion proteins described above can also be used for quantification of binding using antibodies against the GST moiety. Other useful epitope tags include myc-epitopes (e.g., see Ellison et al., *J Biol Chem* 266:21150-21157 (1991)) which includes a 10-residue sequence from c-myc, as well as the pFLAG system (International Biotechnologies, Inc.) or the pEZZ-protein A system (Pharamacia, N.J.).

Compositions

Pharmaceutical compositions includes one or more of the MNTF peptides or analogs thereof disclosed herein together with a pharmaceutically acceptable diluent and/or carrier. Suitable carriers/diluents are well known in the art and include saline or other sterile aqueous media, optionally including additional components such as buffer salts and preservatives, or sugars, starches, salts or mixtures thereof.

Compositions containing MNTF peptides may be provided for use in any suitable form appropriate to the protocol of administration and/or the needs of a patient.

The technology described herein includes culture media that are useful for establishing and propagating stem cells, neural progenitor cells, differentiated neural cells and stem-cell derived motor neurons. The media are particularly suitable for the differentiation of stem cells and long-term culture of stem cell derived motor neurons.

The cell culture media are desirably supplemented with morphogens and/or growth factors, and optimized according to the individual cell type desired to be cultured. Such supplementation and optimization are within the ordinary skill in the art. In some embodiments, the cell culture medium may be supplemented with any or all of the following morphogens and/or growth factors at the following approximate levels (or within one significant digit): RA at 0.001-1 mM, Shh or Shh agonist, at 0.001-1 µM, and/or one or more MNTF peptides or analogs thereof at 0.01-250 µg/ml.

The pharmaceutical formulations described herein may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations include water and physiologically acceptable buffered saline solutions such as phosphate buffered saline solutions pH 7.0-8.0. Suitable pharmaceutical carriers include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and desired, mixed with auxiliary agents, e.g., lubricants, preservatives, stabilizers, wetting agents, emulsiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation.

Compounds provided herein may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the peptide.

Pharmaceutical compositions are generally formulated for administered for a therapeutic purpose. Pharmaceutical compositions may also include one or more active ingredients such as interferons, antimicrobial agents, anti-inflammatory agents, anesthetics, and the like. Formulations for parenteral administration may include sterile aqueous solutions which may also contain buffers, liposomes, diluents and other suitable additives. Pharmaceutical compositions comprising the peptides provided herein may include penetration enhancers in order to enhance the alimentary delivery of the peptides.

Penetration enhancers may be classified as belonging to one of five broad categories, i.e., fatty acids, bile salts, chelating agents, surfactants and non-surfactants (Lee et al., Critical Reviews in Therapeutic Drug Carrier Systems 8, 91-192 (1991); Muranishi, Critical Reviews in Therapeutic Drug Carrier Systems 7, 1-33 (1990)). One or more penetration enhancers from one or more of these broad categories may be included.

Various fatty acids and their derivatives which act as penetration enhancers include, for example, cabrylic acid, valeric acid, oleic acid, lauric acid, capric acid, myristic acid, palmitic acid, stearic acid, linoleic acid, linolenic acid, dicaprate, tricaprate, recinleate, monoolein (a k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Lee et al., Critical Reviews in Therapeutic Drug Carrier Systems page 92 (1991); Muranishi, Critical Reviews in Therapeutic Drug Carrier Systems 7, 1 (1990); El-Hariri et al., J. Pharm. Pharmacol. 44, 651-654 (1992)).

In certain embodiments, exemplary MNTF peptide analogues include functional derivatives of an MNTF peptide with a penetration enhancer, for example one or more fatty acids covalently attached to one or more functional groups on the peptide. In some embodiments, the MNTF peptide analogues include peptides depicted in SEQ ID NOs: 1-22 further having an N-terminal modification with a penetration enhancer, for example a fatty acid and/or alkylcarbonyl (Alk-C(O)—) of from 2 to about 22 carbon atoms, and/or functional derivatives of an MNTF peptide with a protecting group selected from the group consisting of benzyloxycarbonyl, tert-butyloxycarbonyl, fluorenyl-methoxycarbonyl and allyloxycarbonyl, and Y is OH or $NH_2$. In some embodiments, the alkylcarbonyl contains 10 to 20, 12 to 18, or 2-22 carbons. In certain embodiments, suitable N-terminal modification on the MNTF peptide analogue is by palmitylation (e.g. palmitic acid).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al. McGraw-Hill, New York, N.Y., pages 934-935 (1996)). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems page 92 (1991); Muranishi, Critical Reviews in Therapeutic Drug Carrier Systems 7, 1-33 (1990); Buur et al., J. Control Rel. 14, 43-51 (1990)). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems page 92 (1991)); and perfluorochemical emulsions, such as FC-43 (Takahashi et al., *J. Pharm. Phamacol.* 40, 252-257 (1988)). Non-surfactants include, for example, unsaturated cyclic ureas, 1-alkyl- and 1-alkenylazacyclo-alkanone derivatives (Lee et al., Critical Reviews in Therapeutic Drug Carrier Systems page 92 (1991)); and non-steroidal anti-inflammatory agents such as diclofenac sodium, indomethacin and phenylbutazone (Yamashita et al., J. Pharm. Pharmacol. 39, 621-626 (1987)).

Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions provided herein may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition described herein, such as dyes, flavoring agents, preservatives, antioxidants, opacifiers, thickening agents and stabilizers. However, such materials, when added, should not unduly interfere with the biological activities of the components of the compositions provided herein.

Regardless of the method by which compounds are introduced into a patient, colloidal dispersion systems may be used as delivery vehicles to enhance the in vivo stability of the peptides and/or to target the peptides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:peptide complexes of uncharacterized structure. An example of a colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 6, 698-708 (1995)).

In certain embodiments, MNTF peptides and MNTF analogs can be incorporated into or used in conjunction with a biodistribution directing moiety, including one or more polymer, to direct the biodistribution of the MNTF peptide or MNTF analog or other compound provided herein to the proximity of the a desired target or to allow for continuous release of thereof. Active agents include, for example, compounds useful for increasing therapeutic efficacy, for optimizing biodistribution and bioavailability, for reducing tissue damage, for promoting healing, or for increasing patient comfort; exemplary active agents include vasoactive agents, anesthetics, therapeutic agents for ischemia, growth factors and cytokines. Alternatively, microparticulate or nanoparticulate polymeric bead dosage forms may be used in composition provided herein. Compounds provided herein may be used in combination with an active agent and encapsulated in a particulate dosage form with a number of ligand or anti-ligand molecules attached thereto.

In this manner, MNTF peptides and MNTF analogs, and other compounds provided here, alone or in combination with other active agents, are released at that site over time to provide a sustained therapeutic benefit. Sustained release dosage forms are also useful with regard to other active agents useful in the methods described herein, such as growth factors, cytokines, and the like. Release of the active agent from the particulate dosage forms can occur as a result of both diffusion and particulate matrix erosion. Biodegradation rate directly impacts active agent release kinetics.

In certain embodiments, controlled release parenteral formulations of MNTF peptides, MNTF analogs, and compounds described herein can be made as implants, oily injections, or as particulate systems. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Liposomes can be used for controlled release as well as drug targeting of entrapped drug.

In certain embodiments, the pharmaceutical composition described herein, including MNTF peptides and MNTF analogs, can be administered locally, topically, nasally, orally, gastrointestinally, intrabronchially, intravesically, intravaginally, into the uterus, subcutaneously, intramuscularly, periarticularly, intraarticularly, into the cerebrospinal fluid (ICSF), into the brain tissue (e.g. intracranial administration), into the spinal medulla, into wounds, intraperitoneally or intrapleurally, or systemically, e.g. intravenously, intraarterially, intraportally or into the organ directly.

A variety of catheters and delivery routes can be used to achieve intracoronary delivery, as is known in the art. For example, a variety of general-purpose catheters, as well as modified catheters, suitable for use as described herein are available from commercial suppliers such as Advanced Cardiovascular Systems (ACS), Target Therapeutics and Cordis. Also, where delivery to the myocardium is achieved by injection directly into a coronary artery, a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. Detailed descriptions of these and other techniques can be found in the art (see, e.g., Topol, E J (ed.), The Textbook of Interventional Cardiology, 2nd Ed. (W.B. Saunders Co. 1994); Rutherford, R B, Vascular Surgery, 3rd Ed. (W.B. Saunders Co. 1989); Wyngaarden J B et al. (eds.), The Cecil Textbook of Medicine, 19th Ed. (W.B. Saunders, 1992); and Sabiston, D, The Textbook of Surgery, 14th Ed. (W.B. Saunders Co. 1991)).

The compounds provided herein may be administered parentally. Certain compounds are combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intracerebral, intravenous, subcutaneous, or transdermal administration. The formulation which is administered may contain such agents. Examples of these agents include cationic agents (for example calcium phosphate and DEAE-dextran) and lipofectants (for example Lipofectam™ and Transfectam™).

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated gloves, condoms, and the like may also be useful. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral administration may include sterile aqueous solutions which may also contain buffers, diluents and other suitable additives. In some cases it may be more effective to treat a patient with a peptide in conjunction with other traditional therapeutic modalities in order to increase the efficacy of a treatment regimen. As used herein, the term "treatment regimen" is meant to encompass therapeutic, palliative and prophylactic modalities.

Dosing can be dependent on a number of factors, including severity and responsiveness of the disease state to be treated, and with the course of treatment lasting from several days to several months, or until a cure is effected or a diminution of the disease state is achieved. Toxicity and therapeutic efficacy of compounds provided herein can be determined by standard pharmaceutical procedures in cell cultures or experimental animals. For example, for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are useful. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds should be within a range of circulating concentrations that include the $ED_{50}$ with little or no toxicity. The dosage may vary within this range depending upon the dosage form employed and the route of administration utilized. For any compound used as described herein, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Dosing schedules can be calculated from measurements of drug accumulation in the body of the patient. Dosages may vary depending on the relative potency of individual compounds, including MNTF peptides and MNTF analogs, and can generally be estimated based on EC50 s found to be effective in vitro and in in vivo animal models. One of skill in the art will recognize that dosages will vary depending on how and where an MNTF peptide or analog is administered (e.g. in vitro, in vivo, topically, systemically, etc.).

For example, in one aspect, MNTF peptides and MNTF analogs may be administered to achieve from about 0.01 micrograms per ml (μg/mL) to about 1 mg per ml, from about 0.1 μg/mL to about 50 μg/mL, from about 0.1 μg/mL to about 150 μg/mL, from about 1 μg/mL to about 200 μg/mL, and from about 0.1 μg/mL to about 500 μg/mL, including any range within these ranges, final concentrations at a target site (e.g. in a cell culture of ES stem cells).

Alternative suitable dosage amounts may, for example, vary from about 0.1 ug up to a total dose of about 1 gram, depending upon the route of administration. Guidance as to particular dosages and methods of delivery is provided in the literature and generally available to practitioners in the art.

Those skilled in the art will employ different formulations for nucleotides than for proteins or their inhibitors. Similarly, delivery of polynucleotides, polypeptides, and compounds provided herein will be specific to particular cells, conditions, and locations. In general, dosage generally ranges from 0.01 mg/kg to 1000 mg per kg of body weight, and more typically, for example, from 0.1 mg/kg to 300 mg per kg of body weight, and may be given once or more daily, weekly, monthly or yearly, or even once or more during a time span of 2 to 20 years. In certain embodiments, the dosage may be given from immediately post surgery to 24 hours, in another embodiment; the dosage is given from 2 hours and up to 24 hours. Long-acting compositions may be administered every 3 to 4 days, every week, or biweekly depending on the half-life and clearance rate of the particular formulation. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein a selected compound is administered in maintenance doses, ranging from 0.01 mg/kg to 100 mg per kg of body weight, once or more daily, to once every 20 years. In the treatment or prevention of certain conditions, an appropriate dosage level will generally be about 0.001 to 100 mg per kg patient body weight per day which can be administered in single or multiple doses. A suitable dosage level can be about 1 to about 40 mg/kg per day. In certain embodiments, compounds provided herein, including MNTF peptides and analogs thereof, are administered in an amount to achieve in vivo concentrations from about 1 micromolar to about 1 millimolar, from about 10 micromolar to about 500 micromolar, or from about 30 micromolar to about 300 micromolar, and from about 25 micromolar to about 300 micromolar final concentration over the damaged site, and including, about 25 micromolar, or about 220 micromolar, or about 300 micromolar final concentration over the damaged site, and still more typically between about 1 micromolar to about 100 micromolar.

In certain embodiments, dosage of 1, 5, 10, 20, 50, 100, 150, or 200 mg/kg, may be administered.

Compounds described herein can be used in diagnostics, therapeutics, prophylaxis, and as research reagents and in kits. Provision of means for detecting compounds of interest (e.g. MNTF peptides and MNTF analogs) can routinely be accomplished. Such provision may include enzyme conjugation, radiolabelling or any other suitable detection systems. Kits for detecting the presence or absence of compounds of interest may also be prepared.

As used herein, spinal cord injuries may include injuries resulting from a tumor, mechanical trauma, and chemical trauma.

In certain aspects, compositions and therapeutic treatment methods comprising administering to a subject a therapeutically effective amount of a MNTF peptide or analog thereof as defined herein, upon injury to a neural pathway, or in anticipation of such injury, for a time and at a concentration sufficient to maintain the neural pathway, including repairing damaged pathways, or inhibiting additional damage thereto, are provided.

In another aspect, the technology described herein includes compositions and therapeutic treatment methods for maintaining neural pathways. Such treatment methods include administering to the subject, upon injury to a neural pathway or in anticipation of such injury, a compound that stimulates a therapeutically effective concentration of an endogenous MNTF.

Aspects and embodiments described herein provide methods for protecting neurons from the tissue destructive effects associated with the body's immune and inflammatory response to nerve injury.

In certain embodiments, methods, compositions and devices for stimulating cellular repair of damaged neurons and neural pathways, including regenerating damaged dendrites or axons, are provided.

In one aspect, the MNTF peptides and analogs thereof described herein are useful in repairing damaged neural pathways of the peripheral nervous system. In particular, MNTFs are useful for repairing damaged neural pathways, including transected or otherwise damaged nerve fibers. Specifically, the MNTFs described herein are capable of stimulating complete axonal nerve regeneration, including vascularization and reformation of the myelin sheath. The MNTF can be provided to the site of injury in a biocompatible, bioresorbable carrier capable of maintaining the MNTF at the site and, where necessary, means for directing axonal growth from the proximal to the distal ends of a severed neuron. For example, means for directing axonal growth may be required where nerve regeneration is to be induced over an extended distance, such as greater than 10 mm. Many carriers capable of providing these functions are envisioned. For example, useful carriers include substantially insoluble materials or viscous solutions prepared as disclosed herein comprising laminin, hyaluronic acid or collagen, or other suitable synthetic, biocompatible polymeric materials such as polylactic, polyglycolic or polybutyric acids and/or copolymers thereof.

In certain embodiments, a MNTF peptide or analog thereof is disposed in a nerve guidance channel which spans the distance of the damaged pathway. The channel acts both as a protective covering and a physical means for guiding growth of a neurite. Useful channels comprise a biocompatible membrane, which may be tubular in structure, having a dimension sufficient to span the gap in the nerve to be repaired, and having openings adapted to receive severed nerve ends. The membrane may be made of any biocompatible, nonirritating material, such as silicone or a biocompatible polymer, such as polyethylene or polyethylene vinyl acetate. The casing also may be composed of biocompatible, bioresorbable polymers, including, for example, collagen, hyaluronic acid, polylactic, polybutyric, and polyglycolic acids. In one embodiment, the outer surface of the channel is substantially impermeable.

In another aspect, MNTF peptides and analogs thereof described herein are useful to protect against damage associated with the body's immune/inflammatory response to an initial injury to nerve tissue. Such a response may follow trauma to nerve tissue, caused, for example, by an autoimmune dysfunction, neoplastic lesion, infection, chemical or mechanical trauma, disease, by interruption of blood flow to the neurons or glial cells, or by other trauma to the nerve or surrounding material. For example, the primary damage resulting from hypoxia or ischemia-reperfusion following occlusion of a neural blood supply, as in an embolic stroke, is believed to be immunologically associated. In addition, at least part of the damage associated with a number of primary brain tumors also appears to be immunologically related. Application of a MNTF peptide or analog thereof, either directly or systemically alleviate and/or inhibit the immunologically related response to a neural injury.

In another embodiment, the technology described herein encompasses use of biologically active species (phylogenetic) variants of any of the MNTF factor recited herein, including conservative amino acid sequence variants, proteins encoded by degenerate nucleotide sequence variants, and MNTF factors sharing the conserved MNTF domains and encoded by a DNA competent to hybridize under standard stringency conditions to a DNA encoding a MNTF factor disclosed herein, including.

The compounds described herein may also be used for research purposes. Thus, the specific hybridization exhibited by the peptides may be used for assays, purifications, cellular product preparations and in other methodologies which may be appreciated by persons of ordinary skill in the art.

Technical and scientific terms used herein have meanings commonly understood by one of ordinary skill in the art to which the present disclosure pertains, unless otherwise defined. Reference is made herein to various methodologies known to those of skill in the art. Publications and other materials setting forth such known methodologies to which reference is made are incorporated herein by reference in their entireties as though set forth in full. Standard reference works setting forth the general principles of recombinant DNA technology include Sambrook, J., et al., Molecular Cloning: A Laboratory Manual, 2d Ed., Cold Spring Harbor Laboratory Press, Planview, N.Y. (1989) and Molecular Cloning: A Laboratory Manual, third edition (Sambrook and Russel, 2001), jointly and individually referred to herein as "Sambrook"; McPherson, M. J., Ed., Directed Mutagenesis: A Practical Approach, IRL Press, Oxford (1991); Jones, J., Amino Acid and Peptide Synthesis, Oxford Science Publications, Oxford (1992); Austen, B. M. and Westwood, O. M. R., Protein Targeting and Secretion, IRL Press, Oxford (1991); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987, including supplements through 2001); PCR: The Polymerase Chain Reaction, (Mullis et al., eds., 1994); Current Protocols in Immunology (J. E. Coligan et al., eds., 1991); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlagsgesellschaft mbH, 1993), Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. jointly and individually referred to herein as Harlow and Lane), Beaucage et al. eds., Current Protocols in Nucleic Acid Chemistry John Wiley & Sons, Inc., New York, 2000); and Agrawal, ed., Protocols for Oligonucleotides and Analogs, Synthesis and Properties Humana Press Inc., New Jersey, 1993); Teratocarcinomas and embryonic stem cells: A practical approach (E. J. Robertson, ed., IRL Press Ltd. (1987); Guide to Techniques in Mouse Development (P. M. Wasserman et al. eds., Academic Press (1993); Embryonic Stem Cell Differentiation in vitro (M. V. Wiles, *Meth. Enzymol.* 225:900 (1993); Properties and uses of Embryonic Stem Cells: Prospects for Application to Human Biology and Gene Therapy (P. D. Rathjen et al., *Reprod. Fertil. Dev.,* 10:31 (1998)); CNS Regeneration: Basic Science and Clinical Advances, M. H. Tuszynski & J. H. Kordower, eds., Academic Press, (1999).

Certain techniques that may be useful in the practice of the technology disclosed herein are described in various patents and patent applications, including U.S. Pat. No. 5,851,832, which reports multipotent neural stem cells obtained from brain tissue, U.S. Pat. No. 5,766,948 which reports producing neuroblasts from newborn cerebral hemispheres, U.S. Pat. Nos. 5,654,183 and 5,849,553 which report the use of mammalian neural crest stem cells, U.S. Pat. No. 6,040,180 which reports in vitro generation of differentiated neurons from cultures of mammalian multipotential CNS stem cells, WO 98/50526 and WO 99/01159 which report generation and isolation of neuroepithelial stem cells, oligodendrocyte-astrocyte precursors, and lineage-restricted neuronal precursors, and U.S. Pat. No. 5,968,829 which reports neural stem cells obtained from embryonic forebrain and cultured with a medium comprising glucose, transferrin, insulin, selenium, progesterone, and several other growth factors.

Any suitable materials and/or methods known to those of skill can be utilized in carrying out the technology described herein; however, non-limiting examples of materials and/or methods are described herein.

The technology disclosed herein may be appreciated in certain aspects with reference to the following examples, offered by way of illustration, not by way of limitation. Materials, reagents and the like to which reference is made in the following examples are obtainable from commercial sources, unless otherwise noted.

As used herein, it is contemplated that the efficacy of the MNTF peptides and sequence and/or functional analogs thereof may be determined by substantially similar and/or identical protocols as described in the following examples. In addition, it is contemplated that the efficacy of any of the MNTF peptides as set forth in SEQ ID NOs: 1-22, and analogs thereof, may be determined according to the experimental conditions as set forth herein.

Example 1

Testing of MNTF peptide or analog thereof efficacies to attenuate cell death in an in vitro rat motor neuron cell survival model.

Example 1 illustrates the ability of the 6 amino acid analog (GM6) and various shorter peptide analogs of Motoneuronotrophic factor (MNTF) to attenuate cell death in an in vitro rat motor neuron cell survival mode. Administration of GM6 (SEQ ID NO:2) and other analogs (3-mer, 4-mer, 5-mer) at 10 microgram/ml, demonstrated an attenuation of motor neuron cell death which was analog specific. The analogs showed a unique pattern of trophic effect with the analogs containing the terminal phenylalanine as the most efficacious. These data indicate that GM6 and some of the analogs are effective trophic factors in the motor neuron cell survival model.

Abbreviations/Terminology for this Example.

"GM6" and "6mer" mean exemplary 6 amino acid peptide analog of MNTF

"Genervon" and "GB" mean Genervon Biopharmaceuticals, LLC.

"I.V." means intravenous.

"NTS" means Neurological Testing Service, which is a contract research organization.

GM6 is a synthesized 6 amino acid peptide. GM6 was provided as a solid and formulation was prepared by NTS (solution stored at 4° C.). GM6 analogs include sequence homologs of the GM6 peptides.

"PD" means Parkinson's disease

"BDNF" means Brain derived neurotrophic factor

"GDNF" means Glial derived neurotrophic factor

"CNTF" means Ciliary neurotrophic factor

"Genervon" means Genervon Biopharmaceuticals, LLC

"GB" means Genervon Biopharmaceuticals, LLC

Methods and Materials

Purification and culture of motor neurons. Spinal motor neuron cultures were prepared from E14.5 Sprague-Dawley rats (Charles River Labs). Briefly, dissected spinal cords were digested in 0.025% trypsin (Gibco) for 8 min at 37° C. The tissue was transferred to a solution containing L-15 medium (Gibco) supplemented with 2% horse serum (Gibco), insulin (5 µg/ml); putrescine (1×10-4 M), conalbumin (100 µg/ml), sodium selenite (3×10-8 M), progesterone (2×10-8 M), glucose (3.6 mg/ml), penicillin (100 IU/ml), streptomycin (100 µg/ml), DNAse (100 µg/ml) and bovine serum albumin (BSA; 0.4%). The tissue was then triturated using a 1-ml pipetman and the suspension was layered over a cushion of 10.4% Optiprep (Nycomed Pharma) in L-15 in a 15-ml Falcon tube. The layered suspension was centrifuged at 830×g for 15 min. The cells at the interface were suspended in PBS containing 0.5% BSA and separated by immunoaffinity using the IgG-192 p75-specific antibody followed by cell sorting using magnetic microbeads (Miltenyi Biotec) to purify the motor neurons. The motor neurons medium consists of neurobasal medium (Gibco) supplemented with B27 supplement (Gibco), glutamate (25 µM), 2-mercaptoethanol (25 µM) and 2% horse serum. The motor neurons were plated onto laminin-coated coverslips at a density of 3000 cells/coverslip unless otherwise stated. A cocktail of neurotrophic factors (NTFs: 1 ng/ml BDNF, 100 pg/ml GDNF, 10 ng/ml CNTF) was added at the time of cell seeding. After 24 h in culture, motor neurons were treated by addition of the different analogs diluted in motor neurons medium lacking NTFs.

Survival assay. Spinal motor neurons were prepared from E14.5 rat embryos as described. Cells were cultured in the presence of NTFs for 24 h and viability (VI) was estimated by counting the number of calcein AM-positive cells. For viability studies, motor neurons were cultured in the absence of NTFs with the addition of the analogs or GM6. The percentage of viable motor neurons was calculated by counting the number of neurons.

Statistical analysis. The number of surviving motor neurons for each treatment was expressed as a percentage of the number of motor neurons surviving in the presence of NTFs alone (control). Five dishes were used for each condition. Differences between treatments were analyzed for their statistical significance by one-way ANOVA with post hoc Tukey's testing.

Treatment groups. All groups were subjected to GM6, analogs or were controls.

| GM6 | 2309 | 2308 | 2307 | 2312 | 2311 | 2310 | 3223 | 3222 | 3221 | No NTF |
|---|---|---|---|---|---|---|---|---|---|---|

Results

Cell Survival. The trophic efficacy of GM6 and analogs was assessed in an in vitro rat motor neuron cell survival model. The number of surviving motor neurons for each treatment was expressed as a percentage of the number of motor neurons surviving in the presence of NTFs alone (control). The data is summarized in Table 1 and FIG. 1.

TABLE 1

Summary of MNTF peptides and their trophic efficacy in motor neuron survival.

| CS catalog# | SEQ ID NO: | MN survival (% Ctrl) | P value |
|---|---|---|---|
| GM6(GMP014) | SEQ ID NO: 2 | 94.02 ± 3.53 | <0.0001 |
| 2309 | SEQ ID NO: 12 | 81.5 ± 4.50 | <0.0001 |
| 2308 | SEQ ID NO: 6 | 66.38 ± 5.86 | 0.00012 |

TABLE 1-continued

Summary of MNTF peptides and their trophic efficacy in motor neuron survival.

| CS catalog# | SEQ ID NO: | MN survival (% Ctrl) | P value |
|---|---|---|---|
| 2307 | SEQ ID NO: 4 | 35.00 ± 5.28 | 0.017 |
| 2312 | SEQ ID NO: 17 | 12.02 ± 2.31 | 0.69 |
| 2311 | SEQ ID NO: 18 | 9.66 ± 2.50 | 0.39 |
| 2310 | SEQ ID NO: 19 | 12.26 ± 1.70 | 0.70 |
| 3223 | SEQ ID NO: 20 | 15.46 ± 1.82 | 0.73 |
| 3222 | SEQ ID NO: 21 | 10.64 ± 1.72 | 0.46 |
| 3221 | SEQ ID NO: 22 | 9.08 ± 2.32 | 0.33 |
| No NTF | | 13.92 ± 3.42 | N/A |

NA = not applicable
10 µg/mL of each solution is used.

The sets of 3,4,5 mers were produced by solid phase synthesis to represent the metabolites of the 6mer resulting from degradation of the 6mer sequence Phe-Ser-Arg-Tyr-Ala-Arg (SEQ ID No: 2) that takes place starting from N terminal and the C terminal. Amount of peptide in the final product is usually ~80%, water content and acetate ion usually account for ~20%.

Administration of GM6 (SEQ ID NO:2) or analogs containing an N-terminal phenylalanine at 10 µg/ml dose demonstrated protection from neuronal cell loss in culture medium lacking the conventional NTFs. This indicate that GM6 and analogs thereof are effective in sustaining cell survival in the rat motor neuron cell culture and may be beneficial for treating motor neuron related diseases.

All patents, publications, scientific articles, web sites, and other documents and materials referenced or mentioned herein are indicative of the levels of skill of those skilled in the art to which this disclosure pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of some embodiments and are exemplary and not intended as limitations on the scope of the appended claims. Other objects, aspects, and embodiments will occur to those skilled in the art upon consideration of this specification, and are encompassed within the spirit of the disclosure as defined by the scope of the claims. It will be readily apparent to one skilled in the art that varying substitutions and modifications may be made to the technology disclosed herein without departing from its scope and spirit. The technology illustratively described herein suitably may be practiced in the absence of any element or elements, or limitation or limitations, which is not specifically disclosed herein as essential. Thus, for example, in each instance herein, in embodiments or examples of the present technology, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the technology as claimed. Thus, it will be understood that although the present technology has been specifically disclosed by certain embodiments and optional features, modification and variation of the concepts herein disclosed may be resorted to by those skilled in the art, and that such modifications and variations are considered to be within the scope of the invention defined by the appended claims.

The technology has been described broadly and generically herein. Each of the narrower species and subgeneric groupings falling within the generic disclosure also form part of the disclosure. This includes the generic description of the technology with a proviso or negative limitation removing any subject matter from the genus, regardless of whether or not the excised material is specifically recited herein.

Other embodiments are within the following claims. In addition, where features or aspects of the technology are described in terms of Markush groups, those skilled in the art will recognize that the technology is also thereby described in terms of any individual member or subgroup of members of the Markush group.

The invention claimed is:

1. An isolated Motoneuronotrophic Factor (MNTF) peptide or analog thereof consisting of an amino acid sequence set forth in SEQ ID NO:4, SEQ ID NO:6, or SEQ ID NO:12.

2. An isolated Motoneuronotrophic Factor (MNTF) peptide or analog thereof consisting of the amino acid sequence according to SEQ ID NO: 4.

3. An isolated Motoneuronotrophic Factor (MNTF) peptide or analog thereof consisting of the amino acid sequence according to SEQ ID NO: 6.

4. An isolated Motoneuronotrophic Factor (MNTF) peptide or analog thereof consisting of the amino acid sequence according to SEQ ID NO: 12.

5. A composition comprising an MNIF peptide or analog thereof according to claim 1 and a pharmaceutically acceptable carrier.

6. An isolated Motoneuronotrophic Factor (MNTF) analog comprising a Motoneuronotrophic Factor (MNTF) peptide modified by the addition of a penetration enhancer moiety covalently linked to a MNTF peptide to form a heterologous polypeptide, wherein said MNTF peptide portion of said analog consist of an amino acid sequence set forth in SEQ ID NO:4, SEQ ID NO:6, or SEQ ID NO:12.

7. The MNTF analog according to claim 6, wherein said MNTF analog is N-terminally modified by covalent linkage to said penetration enhancer.

8. The MNTF analog according to claim 7, wherein said penetration enhancer is covalently attached to said MNTF peptide or analog thereof by N-acyl derivitization of one or more free amino groups.

9. The MNTF analog according to claim 6, wherein said penetration enhancer is a substituted or unsubstituted alkyl carboxylic acid of 2 to 22 carbons, wherein said alkyl carboxylic acid may be hydroxylated, unsaturated, and/or sulfurated.

10. The MNTF analog according to claim 9, wherein said penetration enhancer is a fatty acid is selected from cabrylic acid, oleic acid, lauric acid, capric acid, caprylic acid, hexanoic acid, myristic acid, palmitic acid, valeric acid, stearic acid, linoleic acid, linolenic acid, arachidonic acid, oleic acid, elaidic acid, erucic acid, and nervonic acid.

11. The MNTF analog according to claim 6, wherein said MNTF analog is synthesized in vitro as one heterologous polypeptide having an MNTF moiety linked covalently to a penetration enhancer moiety.

* * * * *

SEQUENCE LISTING

```
<160> NUMBER OF SEQ ID NOS: 24

<210> SEQ ID NO 1
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Syntheticpolypeptide"

<400> SEQUENCE: 1
```

```
Leu Gly Thr Phe Trp Gly Asp Thr Leu Asn Cys Trp Met Leu Ser Ala
1               5                   10                  15

Phe Ser Arg Tyr Ala Arg Cys Leu Ala Glu Gly His Asp Gly Pro Thr
            20                  25                  30

Gln

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Phe Ser Arg Tyr Ala Arg
1               5

<210> SEQ ID NO 3
<211> LENGTH: 2
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Phe Ser
1

<210> SEQ ID NO 4
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Phe Ser Arg
1

<210> SEQ ID NO 5
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ala Phe Ser
1

<210> SEQ ID NO 6
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 6

Phe Ser Arg Tyr
1

<210> SEQ ID NO 7
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ser Ala Phe Ser
1

<210> SEQ ID NO 8
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ala Phe Ser Arg
1

<210> SEQ ID NO 9
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Leu Ser Ala Phe Ser
1               5

<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ser Ala Phe Ser Arg
1               5

<210> SEQ ID NO 11
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ala Phe Ser Arg Tyr
1               5
```

```
<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Phe Ser Arg Tyr Ala
1               5

<210> SEQ ID NO 13
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Met Leu Ser Ala Phe Ser
1               5

<210> SEQ ID NO 14
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Leu Ser Ala Phe Ser Arg
1               5

<210> SEQ ID NO 15
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Ala Phe Ser Arg Tyr
1               5

<210> SEQ ID NO 16
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ala Phe Ser Arg Tyr Ala
1               5

<210> SEQ ID NO 17
<211> LENGTH: 5
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Arg Tyr Ala Arg
1               5

<210> SEQ ID NO 18
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Arg Tyr Ala Arg
1

<210> SEQ ID NO 19
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Tyr Ala Arg
1

<210> SEQ ID NO 20
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Arg Tyr Ala
1

<210> SEQ ID NO 21
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Arg Tyr Ala
1

<210> SEQ ID NO 22
<211> LENGTH: 3
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 22

Ser Arg Tyr
1

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Trp Met Leu Ser Ala Phe Ser
1               5

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Met Leu Ser Ala Phe Ser Arg Tyr Ala Arg
1               5                   10
```